United States Patent
Nguyen et al.

(10) Patent No.: US 11,129,787 B2
(45) Date of Patent: Sep. 28, 2021

(54) COSMETIC COMPOSITIONS CONTAINING OXAZOLINE FUNCTIONALIZED POLYMERS AND POLYAMINE COMPOUNDS

(71) Applicant: L'OREAL, Paris (FR)

(72) Inventors: Nghi Van Nguyen, Edison, NJ (US); Jim Singer, South Orange, NJ (US); XianZhi Zhou, Millburn, NJ (US); Jennifer Haghpanah, Newtown, CT (US); Charles Shaw, Seattle, WA (US)

(73) Assignee: L'OREAL, Paris (FR)

( * ) Notice: Subject to any disclaimer, the term of this patent is extended or adjusted under 35 U.S.C. 154(b) by 103 days.

(21) Appl. No.: 16/118,717

(22) Filed: Aug. 31, 2018

(65) Prior Publication Data
US 2020/0069555 A1  Mar. 5, 2020

(51) Int. Cl.
*A61K 8/81* (2006.01)
*A61K 8/41* (2006.01)
*A61Q 5/12* (2006.01)
*A61Q 5/00* (2006.01)

(52) U.S. Cl.
CPC ............... *A61K 8/817* (2013.01); *A61K 8/41* (2013.01); *A61Q 5/002* (2013.01); *A61Q 5/12* (2013.01); *A61K 2800/594* (2013.01); *A61K 2800/884* (2013.01); *A61K 2800/95* (2013.01)

(58) Field of Classification Search
CPC ........ A61K 2800/594; A61K 2800/884; A61K 2800/95; A61K 8/41; A61K 8/817; A61K 9/49; A61Q 5/002; A61Q 5/12
See application file for complete search history.

(56) References Cited

U.S. PATENT DOCUMENTS

| 4,722,958 A * | 2/1988 | Sauer ............ A61Q 19/00 524/379 |
|---|---|---|
| 4,867,966 A | 9/1989 | Grollier et al. |
| 5,275,810 A | 1/1994 | Dupuis et al. |
| 8,535,697 B2 | 9/2013 | Inomata et al. |
| 2008/0152909 A1 | 6/2008 | Kyotani et al. |
| 2009/0169502 A1 * | 7/2009 | Quadir ............ A61Q 5/004 424/70.9 |
| 2010/0209375 A1 | 8/2010 | Deboni et al. |
| 2011/0300296 A1 | 12/2011 | Sherman et al. |
| 2013/0034509 A1 | 2/2013 | Cassin et al. |
| 2014/0139595 A1 | 5/2014 | Hong et al. |
| 2016/0256364 A1 | 9/2016 | Dihora et al. |
| 2016/0256365 A1 | 9/2016 | Dihora et al. |
| 2017/0000723 A1 | 1/2017 | Kamei |
| 2017/0002293 A1 | 1/2017 | Dihora et al. |
| 2017/0002302 A1 | 1/2017 | Dihora et al. |
| 2017/0071835 A1 | 3/2017 | Schelges et al. |
| 2017/0071837 A1 | 3/2017 | Schelges et al. |
| 2017/0071842 A1 | 3/2017 | Schelges et al. |
| 2017/0071846 A1 | 3/2017 | Schelges et al. |
| 2017/0073621 A1 | 3/2017 | Schelges |
| 2017/0273877 A1 | 9/2017 | Sasaki et al. |

FOREIGN PATENT DOCUMENTS

| EP | 1948123 B1 | 10/2011 | |
|---|---|---|---|
| EP | 2868309 B1 | 5/2019 | |
| JP | 11279035 A2 | 10/1999 | |
| JP | 2004339496 A | 12/2004 | |
| JP | 2008189907 A | 8/2008 | |
| JP | 2011208129 A | 10/2011 | |
| JP | 2012149147 A | 8/2012 | |
| JP | 5262376 B2 | 8/2013 | |
| JP | 2017025044 A | 2/2017 | |
| JP | 2017179121 A | 10/2017 | |
| WO | WO 1998/014164 * | 4/1998 | ............... A61K 7/06 |
| WO | 2007058382 A1 | 5/2007 | |
| WO | 2011074135 A1 | 6/2011 | |
| WO | 2012099110 A1 | 7/2012 | |
| WO | 2016049456 A1 | 3/2016 | |
| WO | 2016084971 A1 | 6/2016 | |
| WO | 2017044084 A1 | 3/2017 | |

OTHER PUBLICATIONS

Non-Final Office Action for counterpart U.S. Appl. No. 16/118,768, dated Aug. 4, 2020.
Non-Final Office Action for counterpart U.S. Appl. No. 16/118,669, dated Aug. 5, 2020.
Final Office Action for copending U.S. Appl. No. 16/118,768, dated Jan. 8, 2021.
Final Office Action for copending U.S. Appl. No. 16/118,669, dated Jan. 8, 2021.

* cited by examiner

*Primary Examiner* — Anna R Falkowitz
(74) *Attorney, Agent, or Firm* — The Marbury Law Group, PLLC

(57) ABSTRACT

Disclosed are compositions, systems and methods for treating keratinous fibers such as hair. The compositions and systems comprise an oxazoline functionalized polymer and a polyamine compound. The compositions and methods are employed to improve the quality of the keratinous fibers.

29 Claims, No Drawings

COSMETIC COMPOSITIONS CONTAINING OXAZOLINE FUNCTIONALIZED POLYMERS AND POLYAMINE COMPOUNDS

FIELD OF THE INVENTION

The present invention relates to compositions, agents, and methods for treating keratinous fibers. More particularly, the present invention relates to keratinous fiber treatment compositions that can repair or prevent/minimize damaging effects on keratinous substrates caused by extrinsic and intrinsic factors by providing desirable or improved quality and conditioning, hydrophobicity, repair, and improved mechanical properties of the keratinous fibers, such as hair.

BACKGROUND OF THE INVENTION

The appearance and/or condition of keratinous substrates, for example, keratinous fibers such as hair, skin, nails, and lips, are often affected by both extrinsic and intrinsic factors such as aging. In particular, when keratinous substrates are exposed to environmental conditions, for example, high or low humidity or to ultraviolet radiation from the sun, these substrates can lose many of their desirable properties and even become damaged. Keratinous substrates comprising keratinous fibers, especially hair, are constantly exposed to harsh extrinsic conditions, such as sun, chemical damage, e.g., from detergents in shampoos, bleaching, relaxing, dyeing, and permanent waving, heat, e.g., from hair dryers or curlers, and mechanical stress or wear, e.g., from brushing or grooming activities. In addition, any type of hair can diminish in quality and/or quantity over time by age and/or due to factors such as natural greasiness, sweat, shedded skin cells from the scalp, pollution, dirt, and extreme humidity conditions.

The above-described factors can result in thinning hair and/or hair breakage and/or harm the visual appearance and the feel of the hair, and lead to lank body and decreased volume. For example, hair can dry out and lose its shine or color or become frizzy and less manageable under low and high humidity conditions. Under low humidity conditions, hair can dry out and dried-out hair tends to be less shiny and more brittle. Conversely, under high humidity conditions, hair tends to absorb water, causing hair to lose its shape and become unmanageable and unattractive. In addition, hair fibers can become less strong, thereby breaking easily under stress such as stress induced by pulling, brushing, or combing activities. Furthermore, hair can lose its desirable attributes due to physical stress on the hair such as brushing and application of heat. The magnitude of the consequences of these factors is variable, depending on, for example, the quality of the hair, length, style, and environmental factors. As such, these factors generally result in damage to the keratinous fibers, either by affecting protective materials on the surface of the hair (the cuticle), or by altering the hair fiber internally (the cortex).

More specifically, extrinsic conditions may strip protective materials from the surface of the hair, and/or they may disrupt the organized structure of the hair fibers, called the α-structure, which may be accompanied by a decrease in the tensile strength. Such damage to hair by extrinsic factors is more evident the further the hair fiber has grown from the root, because the hair has been exposed longer to such extrinsic factors. In effect, the hair has what may be called a "damage history" as it grows, i.e., the further from the root, the lower the tensile strength and the greater the breakdown in α-structure that has occurred. As a result, consumers continue to seek products such as hair care and hair cosmetic compositions which protect and enhance the appearance of hair as well as reduce the deleterious effects of adverse environmental conditions, photo-damage, and physical stress. Consumers also desire to use hair chemical treatments such as hair dyes, hair relaxers, perm and wave treatments, hair bleaches/lighteners and highlighting treatments that are less damaging to the hair.

Morphologically, a hair fiber contains four structural units: cuticle, cortex, medulla, and intercellular cement. The cuticle layers are located on the hair surface and consist of flat overlapping cells ("scales"). These scales are attached at the root end and point toward the distal (tip) end of the fiber and form layers around the hair cortex. The cortex comprises the major part of the hair fiber. The cortex consists of spindle-shaped cells, or macrofibrils, that are aligned along the fiber axis. The macrofibrils further consist of microfibrils (highly organized protein units) that are embedded in the matrix of amorphous protein structure. The medulla is a porous region in the center of the fiber. The medulla is a common part of wool fibers but is found only in thicker human hair fibers. Finally, the intercellular cement is the material that binds the cells together, forming the major pathway for diffusion into the fibers.

The mechanical properties of hair are determined by the cortex. A two-phase model for the cortex organization has been suggested. Milczarek et al, Colloid Polym. Sci., 270, 1106-1115 (1992). In this model, water-impenetrable microfilaments ("rods") are oriented parallel with the fiber axis. The microfilaments are embedded in a water-penetrable matrix ("cement"). Within the microfilaments, coiled protein molecules are arranged in a specific and highly organized way, representing a degree of crystallinity in the hair fiber.

Similar to other crystalline structures, hair fibers display a distinct diffraction pattern when examined by wide-angle X-ray diffraction. In normal, non-stretched hair fibers this pattern is called an "alpha-pattern". The alpha-pattern or α-structure of hair is characterized by specific repeated spacings (9.8 Å, 5.1 Å, and 1.5 Å). All proteins that display this X-ray diffraction pattern are called α-proteins and include, among others, human hair and nails, wool, and porcupine quill. When the hair fiber is stretched in water, a new X-ray diffraction pattern emerges that is called a "β-pattern", with new spacings (9.8 Å, 4.65 Å, and 3.3 Å).

Damage to hair may occur in the cuticle and/or the cortex. When normal hair is damaged by heat, chemical treatment, UV radiation, and/or physical/mechanical means, myriad chemical and physical changes are induced in the hair. For example, these damaging processes have been known to produce removal or damage to cuticle scales or to cleave the thioester linkage holding the hydrophobic 18-methyl eicosanoic acid ("18-MEA") layer to hair. Thus, it is commonly observed that undamaged hair exhibits significant hydrophobic character, whereas damaged hair shows significant hydrophilic character due to the removal of surface lipids.

There is a need, therefore, for cosmetic products that are useful in protecting the chemical and physical structure of keratinous fibers from harsh extrinsic conditions and restoring the hair's physical properties to undamaged states following damage by extrinsic conditions. More particularly, there is a need to find materials or compositions or methods that can provide a protective barrier and/or treatment to hair to protect it at the cortex. Such a protective barrier or treatment should not be easily transferred from the substrate over time by normal everyday activity. Non-transfer, wash or water-resistant cosmetic, hair and skin care compositions are sought which have the advantage of forming a deposit which does not undergo even partial transfer to the substrates with which they are brought into contact (for example, clothing). It is also desirable to have compositions that do not easily "run off" or wash off the skin and lips when exposed to water, rain or tears. Accordingly, a product that imparts a protective barrier to the substrate that also is shampoo, wash or water/humidity resistant and non-transferable would be of benefit to the area of cosmetic products. As such, makers of cosmetic products such as hair and skin care products continue to seek materials and ingredients that can provide such benefits. At the same time, long lasting benefits or durability of these benefits are also desirable.

In addition, in today's market, many consumers prefer the flexibility of having products that can be used on hair or skin on different ways. Methods for caring for or non-permanent shaping of keratinous fibers include, for example, brushing, teasing, braiding, the use of hair rollers, and heat styling, optionally with a commercially available hair care and styling products. Non-limiting examples of heat styling include blow drying, crimping, curling, and straightening methods using elevated temperatures (such as, for example, setting hair in curlers and heating, and curling with a curling iron and/or hot/steam rollers and/or flat iron).

There is a need, therefore, for materials, compositions, treatment systems, and methods that result in hair with improved quality or that is less damaged when the hair is exposed to adverse environmental and physical factors and/or when chemically treated. As such, it is also advantageous to find a means for treating damaged keratinous fibers by repairing them, that is to say by intrinsically improving the condition of the keratinous fibers, reducing and/or preventing breakage of the keratinous fibers. At the same time, it is desirable that said materials, compositions, treatment systems, and methods provide durable or long-lasting caring and repair benefits to hair.

To achieve at least one or more of these and other advantages, the present disclosure provides methods of protecting and/or repairing keratinous substrates, for example keratinous fibers chosen from hair, eyelashes and eyebrows, from extrinsic damage, for example caused by heating, UV radiation, chemical treatment or other harsh treatment, by applying to or contacting said keratinous fibers with compositions that include at least one oxazoline functionalized polymer and at least one polyamine compound in various combinations thereof in amounts effective to impart hydrophobicity or increased hydrophobicity to the fiber as well as repair or reduce/prevent damage to or to prevent/minimize breakage of or improve the quality and condition of the keratinous fiber.

Another subject of the invention is the use of the combination at least one oxazoline functionalized polymer and at least one polyamine compound to improve the condition of the keratinous fibers and/or to repair damaged keratinous fibers and/or to prevent or reduce breakage of keratinous fibers.

BRIEF SUMMARY OF THE INVENTION

According to one embodiment, the disclosure relates to compositions for treatment of keratinous fibers comprising at least one oxazoline functionalized polymer and at least one polyamine compound.

According to a further embodiment, the disclosure relates to methods of treating keratinous fibers, the methods comprising applying onto keratinous fibers, a treatment composition(s) or system comprising at least one oxazoline functionalized polymer and at least one polyamine compound.

In yet further embodiments, the disclosure relates to systems for treating keratinous fibers comprising one or two separately-contained treatment compositions, the system including:
 (a) at least one oxazoline functionalized polymer; and
 (b) at least one polyamine compound;
with the proviso that components (a) and (b) are either (i): contained in separate treatment compositions; or (ii) contained together in one treatment composition.

According to a further embodiment, the disclosure relates to methods of treating keratinous fibers, comprising applying to the fibers, systems comprising each of the following components, together or separately, in one or two treatment compositions:
 (a) at least one oxazoline functionalized polymer; and
 (b) at least one polyamine compound;
with the proviso that components (a) and (b) are each contained in two separate treatment compositions or are contained together in one treatment composition.

In various embodiments, the at least one oxazoline functionalized polymer of the compositions, systems, kits, and methods of the present invention may be chosen from a waterborne crosslinker polymer, a granule type, and a mixture thereof.

In various embodiments, the at least one polyamine compound of the compositions, systems, kits, and methods of the present invention may be chosen from non-alkoxylated polyamines, alkoxylated polyamines, or a mixture thereof.

In a further embodiment, the disclosure relates to a kit or an article of manufacture comprising a kit for treating hair comprising one or two separately contained compositions, wherein the compositions include the following components:
 (a) at least one oxazoline functionalized polymer; and
 (b) at least one polyamine compound;
with the proviso that components (a) and (b) are each contained in two separate treatment compositions or are contained together in one treatment composition.

Other features and advantages of the present invention will be apparent from the following more detailed description of the exemplary embodiment which illustrates, by way of example, the principles of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"Active material" as used herein with respect to the percent amount of an ingredient or raw material, refers to 100% activity of the ingredient or raw material.

As used herein, the terms "applying a composition onto keratin fibers" and "applying a composition onto hair" and variations of these phrases are intended to mean contacting the fibers or hair, with at least one of the compositions of the invention, in any manner.

"At least one," as used herein, means one or more and thus includes individual components as well as mixtures/combinations.

The term "comprising" (and its grammatical variations) as used herein is used in the inclusive sense of "having" or "including" and not in the exclusive sense of "consisting only of."

The mole ratio as used herein in the present invention is based on the number of functional amino groups of the polyamine compound to the number of functional oxazoline groups of the oxazoline functionalized polymer.

"Conditioning," as used herein, means imparting at least one of combability, manageability, moisture-retentivity, luster, shine, softness, and body to the hair.

"Durable conditioning," as used herein, means that, following at least one shampoo/washing/rinsing after treatment of keratinous fibers such as hair with the compositions of the present disclosure, treated hair still remains in a more conditioned state as compared to untreated hair. The state of conditioning can be evaluated by measuring and comparing, the ease of combability of the treated hair and of the untreated hair in terms of ease of combing and/or the substantivity of the conditioning agent on the hair and/or the hydrophobicity of hair which can be assessed by contact angle measurements (spread of a water droplet on the surface of the hair).

"Durable hydrophobicity," as used herein, means that, following at least one shampoo/washing/rinsing after treatment of keratinous fibers such as hair with the compositions of the present disclosure, treated hair exhibits significant hydrophobic properties as compared to untreated hair or to hair treated with a non-inventive/comparative composition or material. The state of hydrophobicity of hair can be assessed by contact angle measurements (for example, by the spread of a water droplet on the surface of the hair). Durable hydrophobicity as used herein can also refer to durable frizz control, i.e., the frizziness of hair is controlled even under environmental humidity and/or temperature changes.

"Heating" refers to the use of elevated temperature (i.e., above room temperature such as at or above 30° C.). In one embodiment, the heating in accordance with the present invention may be provided by directly contacting the keratinous fibers with a heat source, e.g., by use of a heating device on the keratinous fibers. Non-limiting examples of heating devices and methods to contact the fibers include employing flat ironing and curling devices using elevated temperatures (such as, for example, setting hair in curlers and heating, and curling with a curling iron and/or hot rollers). In another embodiment, the heating in accordance with the present invention may be provided by heating the at least one keratinous fiber with a heat source which may not directly contact the at least one keratinous fiber. Non-limiting examples of heat sources which may not directly contact the at least one keratinous fiber include heating lamps, blow dryers, hair dryers, hood dryers, heating caps, and steamers.

"A heat-activated" composition, as used herein, refers to a composition which, for example, imparts to at least one keratinous substrate such as a keratinous fiber, a property or a benefit or coating or film that is different or improved over the same composition or coating or film which is not heated during or before or after application of the composition. One example includes a composition which imparts better break stress and/or toughness property to at least one keratinous fiber better than the same composition which is not heated during or before or after application. Another example includes a composition that forms a coating or film on the keratinous fiber when the fiber is heated or exposed to elevated temperatures. Another example includes a composition that forms a coating or film on the keratinous fiber and upon exposure or heating of the treated fiber to heat, imparts one or more additional benefits to the fibers such as hydrophobicity or improved hydrophobicity or long lasting hydrophobicity even after exposure of the fibers to high humidity conditions or such as hair manageability or frizz control/improved frizz control.

"High humidity," as defined herein, refers to atmospheric humidity above 40%.

"Homogeneous" means having the visual appearance of being substantially uniform throughout, i.e., visually appears as a single-phase emulsion and/or dispersion.

"Keratinous fiber," as used herein, includes, human keratinous fibers, and may be chosen from, for example, hair, such as hair on the human head, or hair comprising of eyelashes or hair on the body. "Keratinous fiber" as used herein can also refer to keratinous substrates.

The term "style" or styling" as used herein includes shaping, straightening, curling, or placing a keratin fiber such as hair, in a particular arrangement, form or configuration; or altering the curvature of a keratinous fiber or other substrate; or re-positioning a keratin fiber or other substrate to a different arrangement, form or configuration; or providing/maintaining a hold to the shape or configuration of the keratin fiber. In some embodiments, the hold to the shape of configuration of the fiber may be expressed as an improved bending force property.

The term "treat" (and its grammatical variations) as used herein refers to the application of the compositions of the present invention onto keratinous substrates such as keratinous fibers or hair or skin or to contacting said keratinous substrates with the compositions of the present invention.

The term "repair" (and its grammatical variations) as used herein means that the damaged keratinous fibers such as hair fibers following treatment with the compositions of the present disclosure showed an improvement in tensile properties or strength which are similar to that of natural undamaged hair. The improvement in tensile properties can be determined or assessed by any available means such as by mechanical tests of the fibers and/or by consumer and sensory evaluations of perceivable fiber strengthening and/or physical attributes which have a positive impact on fiber mechanical properties. The term "wash cycle" as used herein, refers to a step or process of washing keratinous fibers and may include treating the fibers with a surfactant-based product (e.g., shampoo or conditioner or body wash) then washing or rinsing the fibers with water. The term "wash cycle" may also include washing or rinsing the fibers with water.

As used with regard to the present disclosure, an "system" for treating keratinous fibers as described herein refers to a combination of at least two compositions that are intended to be used together, e.g. simultaneously or subsequently with application of one following application of another. For example, a hair treatment system for treating the hair may comprise application of one treatment composition to the hair, followed by application of a second treatment composition to the hair.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

It is an object of the present invention to provide materials and compositions and methods which provide both a protective coating or barrier or repairing treatment onto keratinous fibers such as hair and which impart native/undamaged physical properties—such as cortex repair, strength, less breakage, hydrophobicity, ease of combing, conditioning, anti-frizz, etc.—to hair, in particular, damaged hair, as well as impart durable or long lasting physical properties mimicking natural/undamaged hair to damaged hair.

It is also an object of the present invention to provide materials and compositions and methods which protect or repair a keratinous fiber chosen from hair comprising applying to the keratinous fiber the composition(s) or system(s) of the present invention in an amount effective to protect or repair said keratinous fiber before or during or after chemically treating the hair (e.g., dyeing the hair using permanent, semi-permanent or demi-permanent dyeing compositions, bleaching/lightening or lifting the color of hair by chemical oxidizing agents, perming the hair using chemical reducing/oxidizing agents, relaxing the hair using lye and no-lye compositions, straightening the hair using chemical straightening agents).

As such, it is desirable to formulate hair repair strategies to address the need for both surface and cortex repair. It has been surprisingly and unexpectedly discovered that compositions and systems containing the combination of oxazoline functionalized polymers and polyamine compounds, when applied to keratinous fibers such as hair, enhance the properties of hair wherein the combination controls the frizziness of hair, increases the conditioning effect (e.g., smoothness, less damaged feel), increases the humidity resistance or hydrophobicity of hair and ameliorates the condition of hair, especially damaged hair, by improving the appearance and quality of hair (for example, smoother feel, softer feel, less damaged feel, more discipline). Thus, the compositions and systems of the present disclosure can provide a cosmetic treatment such as hair care, hair treatment, and hair styling/shaping products such that the quality of the hair is improved or restored resulting in significantly less frizzy hair, better cosmeticities, feel and appearance, durable hydrophobicity or frizz control, durable conditioning, and less damaged condition of the hair.

The present disclosure relates to compositions for treatment of keratinous fibers comprising at least one oxazoline functionalized polymer and at least one polyamine compound.

In an embodiment, the mole ratio of the oxazoline group(s) of the at least one oxazoline functionalized polymer to the amino group(s) of the at least one polyamine compound is greater than 1.

In an embodiment, the at least one oxazoline functionalized polymer is chosen from waterborne crosslinker polymers such as acrylic-based oxazoline functionalized polymers and styrene/acrylic-based oxazoline functionalized polymer, the granule type, and a mixture thereof.

In an embodiment, the at least one oxazoline functionalized polymer is chosen from 2-Propenoic acid, 2-methyl-, methyl ester, polymer with 4,5-dihydro-2-(1-methylethenyl) oxazole and ethyl 2-propenoate with formula: $(C_6-H_9-N-O\cdot C_5-H_8-O_2\cdot C_5-H_8-O_2)_x$ (EPOCROS WS-300), an oxazoline functionalized polymer commercially available as EPCROS WS-500, styrene·butylacrylate·2-isopropenyl-2-oxazoline·divinyl benzene copolymer with formula: $(C_7-H_{12}-O_2\cdot C_8\cdot C_{10}-H_{10}\cdot-C_6-H_9-N-O)_x$ (EPOCROS K-2020-E AND EPOCROS K-2030-E), a granule type (EPOCROS RPS-1005) and a mixture thereof.

In an embodiment, the at least one oxazoline functionalized polymer is a waterborne crosslinker polymer chosen from an acrylic-based oxazoline functionalized polymer such as 2-Propenoic acid, 2-methyl-, methyl ester, polymer with 4,5-dihydro-2-(1-methylethenyl)oxazole and ethyl 2-propenoate (EPOCROS WS-300), and an oxazoline functionalized polymer commercially available as EPCROS WS-500.

In an embodiment, the at least one oxazoline functionalized polymer is a waterborne crosslinker polymer chosen from styrene/acrylic-based oxazoline functionalized polymer such as styrene·butylacrylate·2-isopropenyl-2-oxazoline·divinyl benzene copolymer (EPOCROS K-2020-E AND EPOCROS K-2030-E).

In an embodiment, the polyamine compound is chosen from non-alkoxylated polyamines.

In various embodiments, the polyamine compound is a non-alkoxylated polyamine chosen from polyvinylamines, aminated polysaccharides, amine substituted polyalkylene glycols, amine substituted polyacrylate crosspolymers, amine substituted polyacrylates, amine substituted polymethacrylates, amine substituted polyesters, polyamino acids, polyalkylamines, diethylene triamine, triethylenetetramine, spermidine, spermine, aminosilicones having at least two amino groups, and a mixture thereof.

In an embodiment, the polyamine compound includes non-alkoxylated polyamines such as polyvinylamines.

In an embodiment, the polyamine compound is vinylamine/vinylformamide copolymer.

In an embodiment, the polyamine compound is chosen from polyalkylamines.

In an embodiment, the polyamine compound is chosen from alkoxylated polyamines.

In various embodiments, the polyamine compound is an alkoxylated polyamine chosen from tetradecyloxypropyl-1, 3-diaminopropane; a C12-14 alkyl oxypropyl-1,3-diaminopropane; a C12-15 allyloxypropyl amine, diamine alkoxylated polyamine compounds, triamine alkylated polyamine compounds, and a mixture thereof.

In an embodiment, the compositions and systems of the present invention contain:
  at least one oxazoline functionalized polymer present in a concentration, by weight, of from about 0.5% to about 10%, or such as from about 0.7% to about 5%, based on the total weight of the composition; and
  at least one polyamine compound present in a concentration, by weight, of from about 0.003% to about 15% or from about 0.004% to about 5%, based on the total weight of the composition.

In an embodiment the mole ratio of the oxazoline group(s) of the at least one oxazoline functionalized polymer to the amino group(s) of the at least one polyamine compound is from between about 1:80 to about 80:1.

In an embodiment the mole ratio of the oxazoline group(s) of the at least one oxazoline functionalized polymer to the amino group(s) of the at least one polyamine compound is greater than 1.

In an embodiment the mole ratio of the oxazoline group(s) of the at least one oxazoline functionalized polymer to the amino group(s) of the at least one polyamine compound is less than 1.

In an embodiment, the mole ratio of the oxazoline group(s) of the at least one oxazoline functionalized polymer to the amino group(s) of the at least one polyamine compound is from between about 80:1 to about 1:80 or from about 70:1 to about 1:70 or from about 60:1 to about 1:60 or from about 50:1 to about 1:50 or from about 60:1 to about 1:60 or from about 70:1 to about 1:1 or from about 1:1 to about 1:70 or from about 60:1 to about 1:1 or from about 1:1 to about 1:60 or from about 50:1 to about 1:1 or from about 1:1 to about 1:50 or from about 40:1 to about 1:1 or from about 1:1 to about 1:40 or from about 30:1 to about 1:1 or from about 1:1 to about 1:30 or from about 20:1 to about 1:1 or from about 1:1 to about 1:20 or from about 15:1 to about 1:1 or from about 1:1 to about 1:15 or from about 10:1 to about 1:1 or from about 1:1 to about 1:10 or from about 65:1 to about 1.5:1 or is at about 75:1, 70:1, 64:1, 50:1, 45:1, 40:1, 35:1, 30:1, 28:1, 26:1, 251, 22:1, 20:1, 18:1, 16:1, 15:1, 12:1, 10:1, 9:1, 8:1, 7:1, 6:1, 5:1, 4:1, 3:1, 2:1, 1.5:1, 1:1.5, 1:2, 1:3, 1:4, 1:5, 1:6, 1:7, 1:8, 1:9, 1:10, 1:12, 1:14, 1:15, 1:16, 1:18, 1:20, 1:22, 1:24, 1:25, 1:26, 1:28, 1:30, 1:35, 1:40, 1:45, 1:50, 1:55, 1:60, 1:64, 1:65, 1:70, or 1:75, including ranges or sub-ranges there between or including all ranges with any of these amounts being endpoints. Preferably, the mole ratio of the oxazoline group(s) of the at least one oxazoline functionalized polymer to the amino group(s) of the at least one polyamine compound is from between about 40:1 to about 2:1 or about 20:1 to about 5:1, including ranges or sub-ranges there between.

In an embodiment the weight proportion of the at least one oxazoline functionalized polymer to the at least one polyamine compound is greater than 1.

In an embodiment the weight proportion of the at least one oxazoline functionalized polymer to the at least one polyamine compound is less than 1.

In an embodiment, the compositions and systems of the present invention include amounts of each of the oxazoline functionalized polymer and the polyamine compound sufficient to impart to the keratinous fibers after application thereto, one or more of hydrophobicity, manageability, and frizz control.

In an embodiment, the hydrophobicity imparted to the keratinous fibers includes a contact angle of greater than 85° or greater than 90°.

In an embodiment, the methods of the present invention involve applying the composition of the present invention onto hair, followed by heating the hair at a temperature from between above room temperature and about 250° C. Said method imparts to the hair after application thereto, one or more of hydrophobicity, manageability, and frizz control.

In an embodiment, the methods of the present invention impart a hydrophobicity or improved hydrophobicity to the hair resulting in a contact angle of greater than 85°.

In an embodiment, the methods of the present invention provide hydrophobicity or improved hydrophobicity to the hair that confers high humidity curl retention after a period of exposure to humidity ranging from about 40% to 90%.

In various embodiments, the hydrophobicity imparted to the hair is durable, i.e., the hair remains hydrophobic even after one or more wash cycles.

The present invention also relates to systems for treating a keratinous fiber comprising one or two separately-contained treatment compositions, the system including:
(a) at least one oxazoline functionalized polymer; and
(b) at least one polyamine compound;
with the proviso that either (a) and (b) are each contained in two separate treatment compositions or (a) and (b) are contained in one treatment composition; and wherein when (a) and (b) are combined, the mole ratio of the oxazoline group(s) of the at least one oxazoline functionalized polymer to the amino group(s) of the at least one polyamine compound is greater than 1 or is greater than 2 or ranges from between about 40:1 to about 2:1.

In an embodiment, the composition of the present invention comprises two separately contained compositions:
(1) a first treatment composition containing: at least one oxazoline functionalized polymer in an amount, by weight, of from about 0.1% to about 20%, or from about 0.5% to about 10%, or from about 0.7% to about 5%, based on the total weight of the first treatment composition; and at least one solvent; and
(2) a second treatment composition containing: at least one polyamine compound, in an amount, by weight, of from about 0.04% to about 20%, or from about 0.05% to about 15%, or from about 0.09% to about 10%, based on the total weight of the second treatment composition; and at least one solvent;
wherein upon mixing (1) and (2) or upon applying (1) and (2) in a sequential or layer by layer manner onto keratinous fibers, the mole ratio of the oxazoline group(s) of the at least one oxazoline functionalized polymer to the amino group(s) of the at least one polyamine compound ranges from about 1:80 to about 80:1.

In one embodiment, the present invention relates to a method of treating keratinous fibers, wherein the method is a two-step process comprising the steps of: applying the above-described first treatment composition onto the fibers; and applying the above-described second treatment composition onto the fibers; and optionally, heating the fibers at a temperature above room temperature; wherein the keratinous fibers include hair.

In an embodiment, the composition of the present invention comprises one treatment composition containing: at least one oxazoline functionalized polymer in an amount, by weight, of from about 0.7% to about 5%, based on the total weight of the treatment composition; at least one polyamine compound in an amount, by weight, of from about 0.09% to about 3%, based on the total weight of the treatment composition; and at least one solvent; wherein the mole ratio of the oxazoline group(s) of the at least one oxazoline functionalized polymer to the amino group(s) of the at least one polyamine compound ranges from about 1:80 to about 80:1. In one embodiment, the present invention relates to a method of treating keratinous fibers, comprising applying the treatment composition onto the fibers; wherein the keratinous fibers include hair; and optionally, heating the fibers at a temperature above room temperature.

Without being bound to any one theory, it is believed that the oxazoline functionalized polymers and polyamine compounds, react with each other and to the keratinous substrate via crosslinking reactions when the polymers or compositions containing the polymers are applied onto keratinous substrates such as hair. It is also believed that heat activation or exposing a keratinous substrate such as hair that has been contacted with the compositions or oxazoline functionalized polymers and polyamine compounds of the invention to heat or temperatures above room temperature enhance the kinetics of the crosslinking reactions, thereby resulting in decreasing the time required to impart cosmetic and hydrophobicity/manageability/repair attributes to the hair. It is also believed that heat activation improves the adhesion and cohesion properties of films or coatings formed on the hair. The improved adhesion and cohesion properties result in long-lasting benefits to the hair that withstand shampooing or washing.

The present invention is thus directed to compositions, methods, and systems employing of oxazoline functionalized polymers and polyamine compounds in various combinations thereof, which provide a durable or long-lasting coating on the surface of damaged keratinous substrates such as hair fibers, provide mechanical strength to the fibers that leads to repaired/reinforced fibers that are able to withstand day-to-day grooming, and provide hydrophobicity/conditioning/combability properties to the keratinous substrates, such as hair fibers.

Oxazoline Functionalized Polymer

The at least one oxazoline functionalized polymer of the present invention is a reactive polymer.

As used herein, the term "reactive polymer" is intended to mean any polymer having at least one moiety or chemical functional group which can chemically react with another substance or compound or polymer.

As used herein, the term "polymer" here means a molecule having repeating units. Preferably, the polymers for use in the compositions of the present invention have a molecular weight of more than 5000, in particular, at least 10,000 (g/mole) and with melting temperature, Tg (° C.) ranging from about −50° C. to about 150° C.

Thus, in accordance with the invention, the oxazoline functionalized polymer which is a reactive polymer has at least one moiety or chemical functional group (in this case, an oxazoline group) which can chemically react with the chemical functional group of another substance or compound or polymer. Such reactions can occur by ring-opening reactions (e.g., amide ester covalent bonding). These reactions can also result in the formation of a film or coating.

The reactive polymer is also capable of forming at least one covalent bond with keratin fibers such as hair. Thus, the reactive polymer preferably has at least one chemical functional group which can form at least one covalent bond with at least one functional group on keratin fibers. As the functional group on the keratin fibers, mention may be made of, for example, —SH, —OH, —COOH, and —NH2.

The chemical functional group may react with the functional group on keratin fibers, either spontaneously or via an activator chosen from temperature, pH, at least one co-reagent, and at least one catalyst chosen from chemical and biochemical catalysts, for instance, an enzyme.

The polymers may be in any type of topology chosen from linear, branched, starburst and hyperbranched (for example, dendrimers) chains, and block, random, and alternating chains. The chemical functional groups may be naturally present on the polymer chain, at the end of the chain, grafted along the main chain or the secondary chains, or on the branches of starburst or hyperbranched polymers.

In one embodiment, the reactive polymer may contain two identical or different chemical functional groups.

Thus, in accordance with the invention, the oxazoline functionalized polymer which is a reactive polymer has at least one moiety or chemical functional group (in this case, an oxazoline group) which can chemically react with at least one functional group on keratin fibers. As the functional group on the keratin fibers, mention may be made of, for example, —SH, —OH, —COOH, and —NH2.

In an embodiment, the oxazoline groups on the reactive polymer, the oxazoline functionalized polymer, can chemically react with chemical functional groups on keratin fibers and with chemical functional groups on a second compound or polymer. In various embodiments in accordance with the present invention, the oxazoline groups on the oxazoline functionalized polymer chemically react with the amino groups on the polyamine compound. At the same, in various embodiments in accordance with the present invention, the oxazoline groups on the oxazoline functionalized polymer and/or the amino groups on the polyamine compound chemically react with chemical functional groups on keratin fibers.

Due to the grafting of the reactive polymer (s) onto keratin fibers, various cosmetic properties can be imparted to the keratin fibers: (i) depending on the type of the reactive polymer (s) and/or (ii) the type of second compound or polymer with which the reactive polymer has reacted with and/or (iii) the product resulting from the reaction between the reactive polymer and the second compound or polymer. Since the reactive polymer (s) (i) or the product (iii) can be firmly fixed on the keratin fibers, the cosmetic properties provided to the keratin fibers can last for a long time.

By way of non-limiting example only, the oxazoline polymers may be obtained by polymerizing monomers having an oxazoline-type functional group (a non-radical-polymerizable functional group) of the following formula (I):

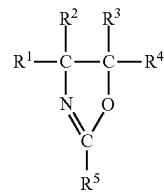

R1, R2, R3, and R4 are independently of each other, hydrogen, a halogen, an alkyl, an aryl, alkoxyalkyl or alkoxyaryl, such as an alkyl group having 1 to 6 carbon atoms, an alkoxyl group having 1 to 6 carbon atoms; R5 is an organic group bearing a radical polymerizable vinyl bond, and when desired, copolymerizing with other one or more kinds of monomers, for example, those bearing a vinyl type of bond. The term "vinyl" with respect to a polymeric material means that the material comprises repeating units derived from vinyl monomers. As used with respect to a vinyl monomer, the term "vinyl" means that the monomer contains a moiety having a free-radically polymerizable carbon-carbon double bond. Monomers having such moieties are capable of copolymerization with each other via the carbon-carbon double bonds.

By way of non-limiting examples, the oxazoline functional monomers of the present invention as represented by the above formula (I) include 2-vinyl-2-oxazoline, 2-vinyl-4-methyl-2-oxazoline, 2-vinyl-4-dimethyl-2-oxazoline, 2-vinyl 4-diethyl-2-oxazoline, 2-vinyl-4-methoxy-2-oxazoline, 2-vinyl-4-ethoxy-2-oxazoline, 2-vinyl-4-methoxymethyl-2-oxazoline, 2-vinyl-4-phenyl-2-oxazoline, 2-vinyl-5-methyl-2-oxazoline, 2-vinyl-5-ethyl-2-oxazoline, 2-vinyl-5-dimethyl-2-oxazoline, 2-vinyl-5-methoxy-2-oxazoline, 2-vinyl-5-ethoxy-2-oxazoline, 2-vinyl-5-methoxymethyl-2- oxazoline, 2-vinyl-5-phenyl-2-oxazoline, 2-vinyl-4-methoxy methyl-5-phenyl-2-oxazoline, 2-isopropenyl-2-oxazoline, 2-isopropenyl-4-methyl-2-oxazoline, 2-isopropenyl-4-dimethyl-2-oxazoline, 2-isopropenyl-4-di-ethyl-2-oxazoline, 2-isopropenyl-4-methoxy-2-oxazoline, 2-isopropenyl-4-ethoxy-2-oxazoline, 2-isopropenyl-4-methoxy-methyl-2-oxazoline, 2-isopropenyl-4-phenyl-2-oxazoline, 2-isopropenyl-5-methyl-2-oxazoline, 2-isopropenyl-5-ethyl-2-oxazoline,2-isopropenyl-5-dimethyl-2-oxazoline, 2-isopropenyl-5-methoxy-2-oxazoline, 2-isopropenyl-5-ethoxy-2-oxazoline, 2-isopropenyl-5-methoxy-methyl-2-oxazoline, 2-isopropenyl-5-phenyl-2-oxazoline, 2-isopropenyl-4-methoxymethyl-5-phenyl-2-oxazoline, and the like as a specific example.

The vinyl monomers can be chosen from, (meth)acrylate monomers, (meth)acrylamide monomers. The term "(meth)acryl" and variations thereof, as used herein, means acryl or methacryl.

The (meth)acrylate monomers may be, by way of non-limiting example, C1-C8 alkyl(meth)acrylates such as methyl(meth)acrylate, ethyl(meth)acrylate, propyl (meth)acrylate, isopropyl(meth)acrylate, butyl(meth)acrylate, tert-butyl(meth)acrylate, pentyl(meth)acrylate, isopentyl(meth)acrylate, neopentyl(meth)acrylate, hexyl(meth)acrylate, isohexyl(meth)acrylate, 2-ethylhexyl(meth)acrylate, cyclohexyl(meth)acrylate, isohexyl(meth)acrylate, heptyl(meth)acrylate, isoheptyl(meth)acrylate, octyl(meth)acrylate, isooctyl(meth)acrylate, allyl(meth)acrylate, and combinations thereof. Additional and non-limiting examples include C1-C8 alkoxy(meth)acrylates, such as methoxy(meth)acrylate, ethoxy(meth)acrylate, propyl oxide(meth)acrylate, isopropyl oxide(meth)acrylate, butyl oxide(meth)acrylate, tert-butyl oxide(meth)acrylate, pentyl oxide(meth)acrylate, isopentyl oxide(meth)acrylate, neopentyl oxide(meth)acrylate. The esters may be, by way of non-limiting example, C2-C6 hydroxy alkyl(meth)acrylates, such as hydroxy ethyl (meth)acrylate, 2-hydroxypropyl(meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth)acrylate, and any combination thereof. The esters may be, by way of non-limiting example, aryl(meth)acrylates such as benzyl(meth)acrylate, phenyl(meth)acrylate, and any combination thereof. The esters can further contain amino groups such as aminoethyl(meth)acrylate, N,N-dimethylaminoethyl(meth)acrylate, N,N-dimethylaminopropyl(meth)acrylate, N,N-dimethylaminodimethylpropyl(meth)acrylate, N,N-diethylaminoethyl(meth)acrylate, and N,N,N-trimethylaminoethyl (meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12)alkyl(meth)acrylates such as N-ethyl(meth)acrylamide, N-t-butyl(meth)acrylamide, N-t-octyl(meth)acrylamide, N-methylol(meth)acrylamide and N-diacetone(meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrenesulfonic, vinylsulfonic, 2-(meth)acryloyloxyethylsulfonic, 2-(meth)acrylamido-2-methylpropylsulfonic acids.

The vinyl monomers can also include the monomers of formulas (II) to (VIII) as described in the PCT publication, WO 2012/099110.

The list of monomers given is not limiting, and it should be understood that it is possible to use any monomer known to those skilled in the art which includes acrylic and/or vinyl monomers (including monomers modified with a silicone chain).

In an embodiment, the oxazoline groups on the reactive polymer (oxazoline functionalized polymer of the present invention) chemically react with chemical functional groups on keratin fibers such as hair and with the functional groups on another compound of the present invention, in this case, the polyamine compound.

In an embodiment, the oxazoline functionalized polymers of the present invention are commercially available under the tradename of EPOCROS, as sold by Nippon Shokubai. In an embodiment, the oxazoline functionalized polymers of the present invention are waterborne cross linker polymers. In an embodiment, the oxazoline functionalized polymers of the present invention are of the granule type.

As used herein, the term "waterborne polymer" means that the polymer is soluble or dispersible or emulsifiable in water.

In an embodiment, when the oxazoline functionalized polymers are chosen from waterborne crosslinker polymers, said polymers include acrylic-based polymers (main component is of the acrylic type) and styrene/acrylic-based polymers (main component is of the styrene/acrylic type).

In an embodiment, the oxazoline functionalized polymers for use in accordance with the present invention are waterborne crosslinker polymer which are reactive with amino groups. The rate of reaction can be increased at temperatures above room temperature.

In an embodiment, the oxazoline functionalized polymers for use in accordance with the present invention are waterborne crosslinker polymers which are reactive with the thiol or hydroxyl group on an aromatic ring, thereby forming amide ester bonds.

For example and without limitation, the at least one oxazoline functionalized polymer is chosen from the oxazoline functionalized polymers sold under the commercial names of EPOCROS WS-300, EPOCROS WS-500, and EPOCROS WS-700 (water-soluble type and acrylic-based), the oxazoline functionalized polymers sold under the commercial names of EPOCROS K-2010-E, K-2020-E, and EPOCROS K-2030-E (emulsion type and styrene/acrylic-based), and a mixture thereof.

The oxazoline functionalized polymer in EPOCROS WS-300 has the chemical name: 2-Propenoic acid, 2-methyl-, methyl ester, polymer with 4,5-dihydro-2-(1-methylethenyl)oxazole and ethyl 2-propenoate, with formula: $(C_6{-}H_9{-}N{-}O \cdot C_5{-}H_8{-}O_2 \cdot C_5{-}H_8{-}O_2)_x$. The oxazoline functionalized polymer in EPOCROS K-2020-E and K-2030-E has the chemical name: styrene·butyl acrylate·2-isopropenyl-2-oxazoline·divinyl benzene copolymer, with formula: $(C_7-H_{12}-O_2 \cdot C_8 \cdot C_{10}-H_{10}·-C_6-H_9-N-O)_x$.

In other examples, the at least one oxazoline functionalized polymer is chosen from the granule type sold under the commercial names of EPOCROS RPS-1005.

The at least one oxazoline functionalized polymer of the present invention may, for example, be present in the composition (one treatment composition or composition resulting from a layer by layer application) containing the at least one oxazoline functionalized polymer and the at least one polyamine compound of the present invention in an amount ranging from about 0.1% to about 20% by weight, such as from about 0.5% to about 10% by weight, or from about 0.7% to about 5% by weight, including all ranges and sub-ranges there between, based on the total weight of the composition.

In various embodiments, the amount of the at least one oxazoline functionalized polymer in the composition (one treatment composition or composition resulting from a layer by layer application) containing the at least one oxazoline functionalized polymer and the at least one polyamine compound of the present invention is about: 0.1%, 0.2%, 0.3%, 0.4%, 0.5%, 0.6%, 0.7%, 0.8%, 0.9%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% by weight, based on the total weight of the composition, including all ranges with any of these amounts being endpoints.

In various embodiments, the at least one oxazoline functionalized polymer of the present invention may, for example, be present in a first treatment composition in an amount ranging from about 0.1% to about 20% by weight, such as from about 0.5% to about 10% by weight, or from about 0.7% to about 5% by weight, including all ranges and sub-ranges there between, based on the total weight of the first treatment composition, including all ranges with any of these amounts being endpoints. For example, the amount of the at least one oxazoline functionalized polymer in the first treatment composition of the present invention is about: 0.1%, 0.2%, 0.3%, 0.4%, 0.5%, 0.6%, 0.7%, 0.8%, 0.9%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% by weight, based on the total weight of the first treatment composition, including all ranges with any of these amounts being endpoints.

Polyamine Compounds

According to various exemplary embodiments of the disclosure, the compositions and systems according to the disclosure comprise at least one polyamine compound.

The polyamine compound of the present disclosure is chosen from non-alkoylated polyamines, alkoxylated polyamines, and mixtures thereof. In certain embodiments, the polyamine compounds of the present disclosure do not contain silicon atoms or silicone moieties.

Non-Alkoxylated Polyamines

The non-alkoxylated polyamines may in particular be chosen from polyvinylamines, aminated polysaccharides, amine substituted polyalkylene glycols, amine substituted polyacrylate crosspolymers, amine substituted polyacrylates, amine substituted polymethacrylates, proteins, protein derivatives, amine substituted polyesters, polyamino acids, polyalkylamines, diethylene triamine, triethylenetetramine, spermidine, spermine, and mixtures thereof. The non-alkoxylated polyamines for use in the present disclosure can also be chosen from aminosilicones having at least two amino groups.

The non-alkoxylated polyamines may be chosen from amine-containing polymers, in particular having a weight-average molecular weight ranging from 500 to 1,000,000, preferably ranging from 500 to 500,000, and preferentially ranging from 500 to 100,000. As amine-comprising polymer, use may be made of polyamines such as poly((C2-C5) alkyleneamines), and in particular polyethyleneimines and polypropyleneimines, especially poly(ethyleneimine)s; poly (allylamine); polyvinylamines and copolymers thereof, in particular with vinylamides; polyamino acids which have $NH_2$ groups; aminodextran; amino polyvinyl alcohol; acrylamidopropylamine-based copolymers; and chitosans.

The non-alkoxylated polyamines of the present disclosure are also preferably chosen from polyvinylamines which are generally sold under the trade name LUPAMINE or LUVIQUAT from BASF. One preferred example of such non-alkoxylated polyamines are polyvinylamines sold under the LUVIQUAT series such as Vinylamine/vinylformamide copolymer (INCI name), sold as LUVIQUAT 9030 by BASF.

The non-alkoxylated polyamines of the present disclosure may also be chosen from Vinylamine/Vinyl Alcohol Copolymer (INCI name).

Other preferred non-alkoxylated polyamines of the present disclosure include are amine substituted polyalkylene glycols such as PEG-15 cocopolyamine and PEG-15 Tallow Polyamine and amine substituted polyacrylate crosspolymer such as the product sold under the name CARBOPOL AQUA CC polymer by Lubrizol Advanced Materials, Inc.

The non-alkoxylated polyamine compound of the present disclosure may also be chosen from proteins and protein derivatives such as wheat protein, soy protein, oat protein, collagen, and keratin protein.

In an embodiment of the present disclosure, the non-alkoxylated polyamine compound is chosen from polyamino acid compounds comprising lysine, compounds comprising arginine, compounds comprising histidine, and compounds comprising hydroxylysine. Non limiting examples include chitosan and polyamino acids such as polyarginine, polyhistidine, polylysine, and mixtures thereof.

Alkoxylated Polyamines

The alkoxylated polyamines of the present disclosure are chosen from amine compounds having at least two amino groups and at least one degree of alkoxylation. The alkoxylation is provided by an alkylene oxide group which is preferably chosen from ethylene oxide and propylene oxide.

Non-limiting preferred examples of suitable alkoxylated polyamines include compounds corresponding to formula (IB):

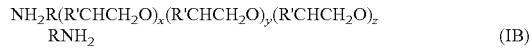

$$NH_2R(R'CHCH_2O)_x(R'CHCH_2O)_y(R'CHCH_2O)_z \\ RNH_2 \quad \text{(IB)}$$

wherein R represents a $—CH_2—$, $—CH_2CH_2—$, $—CHCH_3—$ or $—C(CH_3)_2—$ group, or a hydrocarbon radical containing at least 3 carbon atoms that is linear or branched, acyclic or cyclic, saturated or unsaturated, aliphatic or aromatic, substituted or unsubstituted;

x, y, and z independently of one another, represent numbers of from 0 to about 100;

R' represents hydrogen, or an alkyl group, preferably a methyl group; and the sum of x+y+z is at least 1.

In formula (IB), R is preferably a linear or branched, acyclic alkyl or alkenyl group or an alkyl phenyl group; x, y, and z independently of one another, preferably represent numbers ranging from 2 to 100.

Examples of the alkoxylated polyamines for use in the present disclosure which correspond to formula (IB) include, for example, tetradecyloxypropyl-1,3-diaminopropane; a C12-14 alkyl oxypropyl-1,3-diaminopropane; a C12-15 alkyloxypropyl amine and other similar materials that are commercially available from Tomah under the tradename of TOMAH DA-17.

Other examples of alkoxylated polyamines of Formula (IB) are diamine compounds belonging to the JEFFAMINE series such as the JEFFAMINE D and JEFFAMINE ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. JEFFAMINE D series compounds are amine terminated PPGs (polypropylene glycols) and JEFFAMINE ED series compounds are polyether diamine based with a predominantly PEG (polyethylene glycol) backbone.

Other non-limiting preferred examples of suitable alkoxylated polyamines in the diamine form include compounds corresponding to formula (IIB):

NH$_2$(CH$_2$)$_x$OCH$_2$CH$_2$O(CH$_2$)$_x$NH$_2$     (IIB)

wherein x is 2 or 3.

Examples of alkoxylated polyamines of Formula (IIB) are diamine compounds belonging to the JEFFAMINE series available from Huntsman Corporation, Salt Lake City, Utah, such as JEFFAMINE EDR148, and JEFFAMINE EDR176.

Additional non-limiting preferred examples of alkoxylated polyamines in the triamine form include compounds corresponding to formula (IIIB):

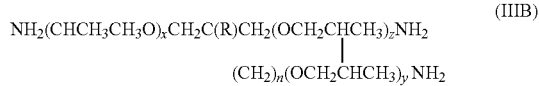

NH$_2$(CHCH$_3$CH$_3$O)$_x$CH$_2$C(R)CH$_2$(OCH$_2$CHCH$_3$)$_z$NH$_2$     (IIIB)
(CH$_2$)$_n$(OCH$_2$CHCH$_3$)$_y$NH$_2$ wherein R is hydrogen, —CH$_2$ or —C$_2$H$_5$,
n=0 or 1, and
x, y, and z independently of one another, represent numbers of from 0 to 100 and the sum of x+y+z is at least 1.

Examples of alkoxylated polyamines for use in the present disclosure which correspond to formula (IIIB) are triamine compounds belonging to the JEFFAMINE series such as the JEFFAMINE T series available from Huntsman Corporation, Salt Lake City, Utah. Examples of the JEFFAMINE T series compounds are JEFFAMINE T403, JEFFAMINE T3000, and JEFFAMINE T5000. JEFFAMINE T series compounds are triamines made by reacting PO with a triol initiator followed by aminating the terminal hydroxyl groups.

Another type of preferred alkoxylated polyamines include compounds of formulas (IVB) and (VB) hereunder:

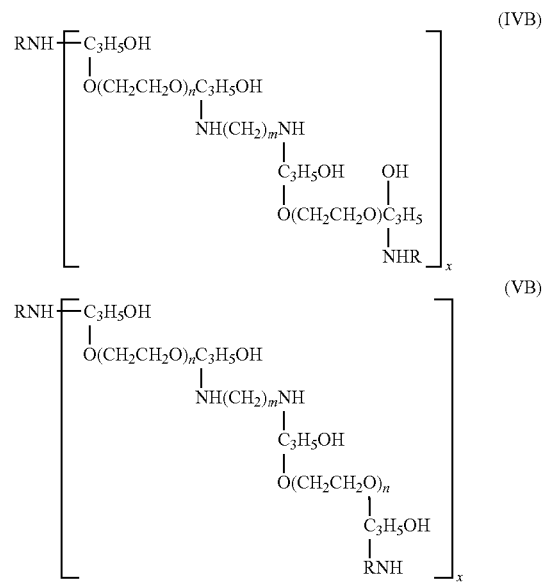

wherein
R in formula (IVB) represents the alkyl group derived from tallow and R in formula (VB) represents the alkyl group derived from coconut oil;
n in both formulas (IVB) and (VB) has a total value ranging from 10 to 20;
m in both formulas (IVB) and (VB) has a value ranging from 2 to 6; and
x in both formulas (IVB) and (VB) has a value ranging from 2 to 4.

One particular triamine alkoylated polyamine compound is JEFFAMINE T-500 polyetheramine of the formula:

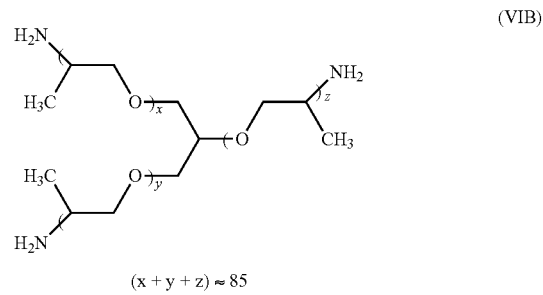

Other preferred types of alkoxylated polyamines include aminosilicones with at least one degree of alkoxylation.

Preferred examples of alkoxylated polyamines for use in the present disclosure include compounds of Formulas (IVB), (VB) and (VIB) above, such as PEG-15 Tallow Polyamine, PEG-15 Cocopolyamine, and JEFFAMINE T-500 polyetheramine, respectively.

In one preferred embodiment of the present disclosure, the polyamine compound of the present disclosure is chosen from polyvinylamines such as Vinylamine/vinylformamide copolymer (INCl name), sold as LUVIQUAT 9030 by BASF; alkoxylated polyamines which correspond to formula (I IIB) such as JEFFAMINE T403, JEFFAMINE T3000, and JEFFAMINE T5000 (in particular, corresponds to formula (VIB); and mixtures, thereof.

The at least one polyamine compound of the present invention may, for example, be present in the composition (one treatment composition or composition resulting from a layer by layer application) containing the at least one oxazoline functionalized polymer and the at least one polyamine compound of the present invention in an amount ranging from about 0.001% to about 20% by weight, such as from about 0.003% to about 5% by weight, from about 0.004% to about 5% by weight, or from about 0.09% to about 3% by weight, including all ranges and sub-ranges there between, based on the total weight of the composition.

In various embodiments, the amount of the at least one polyamine compound in the composition (one treatment composition or composition resulting from a layer by layer application) containing the at least one oxazoline functionalized polymer and the at least one polyamine compound of the present invention is about: 0.002%, 0.004%, 0.005%, 0.006%, 0.008%, 0.01%, 0.013%, 0.014%, 0.016%, 0.017%, 0.02%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.3%, 0.4%, 0.5%, 0.6%, 0.7%, 0,8%, 0.9%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% by weight, based on the total weight of the composition, including all ranges with any of these amounts being endpoints.

In various embodiments, the at least one polyamine compound of the present invention may, for example, be present in a second treatment composition in an amount ranging from about 0.04% to about 20% by weight, such as from about 0.05% to about 15% by weight, or from about 0.09% to about 10% by weight, including all ranges and sub-ranges there between, based on the total weight of the second treatment composition, including all ranges with any of these amounts being endpoints. For example, the amount of the at least one polyamine compound in the second treatment composition of the present invention is about: 0.05%, 0.06%, 0.07%, 0.08%, 0.09%, 0.1%, 0.2%, 0.3%, 0.4%, 0.5%, 0.6%, 0.7%, 0.8%, 0.9%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.2%, 5.4%, 5.5%, 5.6%, 5.8%, 6%, 6.2%, 6.4%, 6.5%, 6.6%, 6.8%, 7%, 7.2%, 7.4%, 7.5%, 7.6%, 7.8%, 8%, 8.2%, 8.4%, 8.5%, 8.6%, 8.8%, 9%, 9.2%, 9.4%, 9.5%, 9.6%, 9.8%, 10%, 12%, 14%, 15%, 16%, 18%, or 20% by weight, based on the total weight of the second treatment composition, including all ranges with any of these amounts being endpoints.

Additional Components

The compositions and systems according to the disclosure may optionally contain additional components and/or additives, such as solvents, hair active agents, conditioning agents, and any additional component suitable for treatment of keratinous fibers according to the disclosure.

Solvents

In various embodiments, the compositions and systems further comprise one or more suitable solvents for treatment of keratinous fibers. Examples of suitable solvents include water, in some particular embodiments distilled or de-ionised water, organic solvents, or mixtures thereof. Exemplary organic solvents may be chosen from volatile and nonvolatile organic solvents.

Suitable organic solvents are typically C1-C4 lower alcohols, glycols, polyols, polyol ethers, hydrocarbons, and oils. Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. In an exemplary embodiment, glycol ether for use in the present invention is dipropylene glycol n-butyl ether, known under the tradename of DOWANOL DPnB.

Suitable organic solvents also include synthetic oils and hydrocarbon oils include mineral oil, petrolatum, and C10-C40 hydrocarbons which may be aliphatic (with a straight, branched or cyclic chain), aromatic, arylaliphatic such as paraffins, iso-paraffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon based oil" or "hydrocarbon oil" refers to oil mainly containing hydrogen and carbon atoms and possibly oxygen, nitrogen, sulfur and/or phosphorus atoms. Representative examples of hydrocarbon based oils include oils containing from 8 to 16 carbon atoms, and especially branched C8-C16 alkanes (also known as isoparaffins), for instance isododecane (also known as 2,2,4,4,6 pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2 phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltri-siloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluoro oils such as nonafluoromethoxybutane and perfluoro methylcyclopentane.

Particularly suitable solvents in the composition of the present disclosure include water, isododecane, ethanol, and combinations thereof. The solvent will typically be present in total amounts ranging from about 60% to 98%, in some particular embodiments from 80% to 96%, by weight, including all ranges and sub-ranges there between, based on the total weight of the composition.

In yet some other embodiments, the solvent of the present disclosure does not comprise water and/or organic solvent that is added as a separate ingredient, by itself, into the compositions of the present invention, such that water and/or organic solvent is present in the compositions of the present invention when it accompanies one or more ingredients of a raw material that is added into the compositions of the invention.

When the compositions of the disclosure contain water, according to various embodiments, water can be present in amounts of about 98% or less, such as about 96%, 95%, 90%, 85%, 80%, 75%, 70%, 65%, 60%, 55%, 50%, 48%, 46%, 45%, 44%, 42%, 40%, 35%, 30%, 20%, 10%, or 5% or less, by weight, based on the total weight of the composition, including all ranges with any of these amounts as endpoints.

When the compositions of the disclosure contain an organic solvent(s), according to various embodiments, the organic solvent(s) can be present in a total amount of about 98% or less, such as about 96%, 95%, 90%, 85%, 80%, 75%, 70%, 65%, 60%, 55%, 50%, 48%, 46%, 45%, 44%, 42%, 40%, 35%, 30%, 20%, 10%, or 5%, or less, by weight, based on the total weight of the composition, including all ranges with any of these amounts as endpoints.

Conditioning Agents and Compositions

The compositions and systems for treating keratinous fibers in accordance with the present disclosure may optionally comprise conditioning compositions or conditioning agents other than the polyamine compounds of the present invention, such as cationic conditioning agents, silicone compounds, and mixtures thereof.

The total amount of the one or more conditioning agents may vary. In some cases, the total amount of the one or more conditioning agents is from about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

In some embodiments, the total amount of the one or more conditioning agents in the composition ranges from about 0.1 to about 5% by weight, about 0.2 to about 4% by weight, about 0.4 to about 3% by weight, about 0.5 to about 2% by weight, or about 0.5 to about 1% by weight, based on the total weight of the conditioning composition, including all ranges and sub-ranges there between. In a particular embodiment, the amount of the silicone compound is at about 0.4%, 0.43%, 0.45%, 5%, 0.55%, 0.57%, 0.65%, 0.7%, 7.75%, 0.78%, 0.8%, 0.85%, 0.9%, 0.95%, 1%, 1.1%, 1.2%, 1.3%, 1.4%, 1.5%, 1.6%, 1.7%, 1.8%, 1.9%, 2%, 2.1%, 2.2%, 2.3%, 0.2.4%, 2.5%, 2.6%, 2.7%, 2.8%, 2.9%, 3%, 3.1%, 3.2%, 3.3%, 3.4%, 3.5%, 3.6%, 3.7%, 3.8% 3.9%, 4% by weight, based on the total weight of the conditioning composition, including all ranges with any of these amounts as endpoints.

Additives

The compositions and systems according to the present disclosure may optionally further include suitable additives for treatment of keratinous fibers. For example, the compositions and systems may also comprise additives chosen from emulsifiers/co-emulsifiers, rheology modifiers, thickening and/or viscosity modifying agents, nacreous agents, opacifiers, fragrances, vitamins, preserving agents, neutralizing agents, pH stabilizers, and mixtures thereof.

Suitable examples of emulsifiers are nonionic surfactants such as alkoxylated fatty alcohols, fatty alcohols, fatty amides, sorbitan derivatives, polyethylene glycol esters (e.g., PEG-100 stearate), and mixtures thereof.

If present in the composition, the above-described additives are generally present in an amount ranging up to about 50% by weight including all ranges and sub-ranges there between, based on the total weight of the composition, such as from about 0.001% to about 50%, or from about 0.001% to about 40%, or from about 0.001% to about 30%, or from about 0.001% to about 20%, or from about 0.001% to about 10%, by weight, based on the total weight of the composition.

Needless to say, a person skilled in the art will take care to select this or these optional additional components or additives, and/or the amount thereof, such that the advantageous properties of the composition, according to the invention, are not, or are not substantially, adversely affected by the envisaged addition.

Compositions, Systems, and Methods of Use

According to various embodiments of the disclosure, the treatment compositions may be a single-composition treatment, or may be a two-composition treatment system. In various embodiments, the present disclosure is also directed to methods of treating hair, the methods comprising applying compositions and systems according to the disclosure onto keratinous fibers such as hair. The treatment process may thus be a one-step or two-step application.

For example, in one exemplary and non-limiting embodiment, the present disclosure is directed to compositions for the treatment of keratinous fibers such as hair, wherein a single composition comprises at least one oxazoline functionalized polymer and at least one polyamine compound. In such embodiments, the composition of the present disclosure is applied onto keratinous fibers such as hair in a one-step application process. The composition for use in a one-step application may be prepared by combining the at least one oxazoline functionalized polymer and the at least one polyamine compound, resulting in a treatment composition that is then applied onto the keratinous fibers.

In yet a further exemplary and non-limiting embodiment, the present disclosure is directed to a system comprising two compositions: (a) a first treatment composition containing at least one oxazoline functionalized polymer; and (b) a second treatment composition containing at least one polyamine compound, wherein (a) and (b) are to be applied sequentially onto hair in any order or are to be combined to form a hair treatment mixture for application onto hair.

In exemplary embodiments, keratinous fibers such as hair are treated in a two-step application process, i.e., the fibers are treated by system comprised of two treatment compositions. In one exemplary and non-limiting embodiment of the two-step application process, two treatment compositions are applied to the keratinous fibers in a step-wise fashion in any order to treat the substrate, wherein a first treatment composition contains the at least one oxazoline functionalized polymer, and a second treatment composition contains the at least one polyamine compound.

In exemplary embodiments, the above-described first or second treatment compositions or hair treatment mixture are heat-activated compositions such that certain cosmetic benefits are imparted to hair fibers when the fibers are heated at a temperature above room temperature before or during or after treating the hair with the said composition(s) or mixture.

As described herein, heating of keratinous fibers may be effected by applying heat to the hair or exposing hair to elevated temperatures or temperatures above room temperature. The temperature of heating can be equal to or above 30° C., equal to or above 40° C., equal to or above 45° C., equal to or above 50° C., equal to or above 55° C., equal to or above 60° C., equal to or above 70° C., equal to or above 80° C., equal to or above 90° C., equal to or above 100° C., equal to or above 125° C., equal to or above 150° C., equal to or above 175° C., equal to or above 200° C., or equal to or above 225° C., including all ranges of temperatures having any of these numbers as endpoints. While not so limited, heating may be provided, for example, by commonly used heating tools for example a heating lamp or helmet dryer or blow dryer (about 30° C. and above, such as from about 30° C. to about 100° C. or from about 40° C. to about 80° C. or from about 40° C. to about 70° C.) or hot iron or flat iron (about 130° C. to about 250° C.) or steam/hot rollers. Heating the hair may be accompanied by the use of a brush or comb or similar device over the fibers or by running the fingers through the fibers. When a flat iron is employed, one or more several passes of the flat iron over the fibers are employed.

In various exemplary embodiments, the weight ratio of the at least one oxazoline functionalized polymer to the at least one polyamine compound in the compositions and systems of the disclosure can range from about 20:1 to 1:2, such as from about 18:1 to about 1:2, about 16:1 to about 1:2, about 15:1 to about 1:2, about 14:1 to about 1:2, about 12:1 to about 1:2, about 10:1 to about 1:2, about 9:1 to about 1:1, about 8:1 to about 1:1, about 7:1 to about 1:1, about 6.5:1 to about 1:1, about 6.25 to about 1:1, about 6:1 to about 1:1, about 5:1 to about 1:1, about 4:1 to about 1:1, about 3:1 to about 1:1, or about 2:1 to about 1:1, including ranges and sub-ranges there between. For example, the weight ratio of the at least one polyamine compound to the oxazoline functionalized polymer is at about: 20, 18, 16, 15, 14, 12, 10, 9.7, 9, 8, 7, 6.9, 6.5, 6.25, 6, 5.5, 6, 5, 4, 4.3, 3, 2, 2.2, 1, 0.9, 0.8, 0.7, 0.6, or 0.5, including all ranges with any of these amounts being endpoints. In certain embodiments, the at least one oxazoline functionalized polymer is present in a greater proportion than the polyamine compound. In certain other embodiments, the at least one oxazoline functionalized polymer is present in a lesser proportion than the polyamine compound.

In various embodiments, the present disclosure is directed to hair treatment systems comprising at least: a first composition containing at least one oxazoline functionalized polymer and a solvent; and a second composition containing at least one polyamine compound and a solvent; wherein the first and the second compositions are each contained in separate containers and wherein the first and the second compositions are applied on hair in a step-wise manner.

In one exemplary embodiment, the first and second treatment compositions above may be applied to keratinous fibers, such as hair, according to a two-step application method comprising steps of:
(i) applying the first treatment composition onto the fibers;
(ii) leaving the first treatment composition on the fibers at room temperature for a certain period of time, such as for at least 30 seconds such as from about 1 to about 60 minutes, or about 40 minutes to about 60 minutes, or for about 10 minutes or about 15 minutes or about 20 minutes or about 25 minutes or about 30 minutes or about 35 minutes or about 40 minutes or about 60 minutes;
(iii) applying the second treatment composition onto the fibers;
(iv) leaving the first treatment composition on the fibers at room temperature for a certain period of time, such as for at least 30 seconds such as from about 1 to about 60 minutes, or about 40 minutes to about 60 minutes, or for about 10 minutes or about 15 minutes or about 20 minutes or about 25 minutes or about 30 minutes or about 35 minutes or about 40 minutes or about 60 minutes; and
(v) optionally, heating the fibers at a temperature above room temperature.

In one exemplary embodiment, the disclosure relates to a single-step treatment composition comprising at least one oxazoline functionalized polymer and a solvent; a second composition containing at least one polyamine compound; and a solvent.

In one exemplary embodiment, the single composition above may be applied to keratinous fibers, such as hair, according to a single-step application method comprising steps of:
(i) applying the treatment composition onto the fibers;
(ii) leaving the first treatment composition on the fibers at room temperature for a certain period of time, such as for at least 30 seconds such as from about 1 to about 60 minutes, or about 40 minutes to about 60 minutes, or for about 10 minutes or about 15 minutes or about 20 minutes or about 25 minutes or about 30 minutes or about 35 minutes or about 40 minutes or about 60 minutes; and
(iii) optionally, heating the fibers at a temperature above room temperature.

In some embodiments, the hair that has been treated with the compositions of the present invention and then heated is rinsed with water and/or a shampoo and or a conditioner.

In at least some embodiments, the compositions and systems for treating keratinous fibers, such as hair fibers, according to the disclosure includes amounts of each of the at least one oxazoline functionalized polymer and the at least one polyamine compound, sufficient to impart to the keratinous fibers after application thereto, one or more of:
hydrophobicity or increased hydrophobicity;
humidity resistance;
increased manageability;
frizz-control or improved frizz control;
durable frizz control;
improved conditioning;
protection from damage caused by extrinsic and/or intrinsic factors;
repair when the keratinous fibers are in a damaged condition;
minimized or no breakage;
increased or improved mechanical strength; or
increased hold to the shape or configuration of the fibers.

The compositions and methods, according to the present disclosure, provides advantageous properties to keratinous fibers. In one embodiment, the compositions and methods, according to the present disclosure, provide or impart hydrophobicity to hydrophilic or damaged keratinous fibers, such as damaged hair (bleached), upon application thereto. In certain embodiments, hydrophobicity is provided at room temperature, i.e., without heating or applying heat to the hair. In other embodiments, the hydrophobicity is provided when heat is used on the hair (before or after applying the composition(s) on the hair or during the application of the composition(s) on the hair).

In one embodiment, the hydrophobicity provided to less hydrophobic or to hydrophilic keratinous fibers includes a contact angle of greater than 85° or greater than 90° or greater than 95° or greater than 100° or greater than 110° or greater than 120° or ranges from between 85° to 140° or from between 90° to 135° or from between 100° to 130°, including ranges and sub-ranges there between.

Further disclosed herein is the use of the compositions of the present disclosure for caring for keratinous fibers, for example, hair, such as for hair repair treatments, or for reducing damage to the hair or for imparting improved strength to hair or reducing/preventing hair breakage.

The compositions of the present disclosure may be employed in an effective amount to adequately cover the surface of the fibers of the hair and to achieve the desired effects of hair repair and conditioning.

An effective amount of the composition is typically from about 0.03 gram to about 50 grams per head of hair, and in some applications for treatment of hair, in amounts from about 5 to 60 grams, and in yet further embodiments for an abundance of hair in amounts from about 10 to about 80 grams or more. It will thus be appreciated that the amounts applied depend on the amount or volume of keratinous fibers, such as hair, to be treated and may thus fall within lower ranges for small amounts or patches of hair to the higher ranges and beyond for large amounts or patches of hair. Typical applications are to the whole head in the case of treatment of hair. It will be understood that application to the hair typically includes working the composition through the hair.

Further disclosed herein is the use of the compositions of the present disclosure for shaping or styling hair and/or retaining a hairstyle. Also disclosed is the use of the compositions of the present disclosure for caring for the hair such as for hair repair treatments, or for reducing damage to the hair or for improving the feel of the hair by imparting hydrophobicity to the hair. The compositions may be applied to wet or dry hair. They may be used in a non-rinse fashion. In some other embodiments, the composition may be rinsed from the hair.

In an embodiment, the hair that has been contacted with the treatment compositions and systems of the present invention is further heated or exposed to elevated temperatures (above room temperature). The heat source can be chosen from a blow dryer, a flat iron, a hair dryer, a heat lamp, a heat wand, or other similar devices.

A smoothing or crimping action may be applied on the hair while heating the hair by use of suitable devices, including a hair brush, comb, or flat iron. The smoothing action on the hair may also include running the fingers through the hair.

In an embodiment, the hair treated with the compositions and systems of the present invention are heated or subjected to heat or elevated temperatures (above room temperature).

A suitable applicator device for contacting the hair with compositions of the present invention is an applicator brush. It will be appreciated that while a brush is an example of a suitable applicator, particularly for hair, other applicators may be used, including but not limited to spray bottles, squeeze bottles, one and two chamber pumps, tubes, combs, and other applicators known in the art.

In addition, independently of the embodiment use, the composition present on the fibers or hair is left in place for a time, generally, from about 30 seconds to about 60 minutes, such as from about 40 to about 60 minutes, or such as from about 5 to about 45 minutes, or such as from about 5 to about 20 minutes, or such as from about 10 to about 20 minutes, or such as of about 20 minutes or such as of about 10 minutes. In alternate embodiments, the treatment times may be longer, and in some embodiments, appreciably longer, such that the application may be left on for up to 24 hours to about 48 hours.

The compositions of the present invention are easy to spread on hair.

It has surprisingly and unexpectedly discovered that the application of the composition onto hair results in less frizzy hair and/or more conditioned hair and/or more humidity resistant hair. It was also surprisingly and unexpectedly discovered that the application of the composition of the present invention onto the hair resulted in improved hair quality, for example, one or more of better hair feel, less frizzy hair, less damaged feel of hair, smoother hair, better hair manageability, or improved appearance of the hair (e.g., healthy look).

The hair care and hair cosmetic effects obtained using the compositions and methods of the present invention may also be durable or long-lasting, i.e., wash or shampoo resistant.

As used herein, "long-lasting" or "durable" is understood to mean that the benefits imparted to hair by the compositions of the invention last over a period of time and/or over high humidity conditions and/or after one or multiple wash cycles (with water or shampoo/water or shampoo/water/ conditioner/water or conditioner/water). The multiple wash cycles is understood to mean one or more wash cycles, such as one or two or three or four or five or six or seven or eight or nine or ten wash cycles.

Instructions for applying the composition of the present invention onto keratinous fibers such as hair on the head may comprise directions of use of the composition for the end-user to follow. The end-user may be a consumer or cosmetologist or salon hair dresser. Directions may comprise instructing the end-user to take an amount of the composition in sufficient quantity such that the composition adequately covers the substrates and imparts the desired effects. Directions may additionally instruct the end-user to use a device (e.g., heating device) to achieve the desired effects.

Instructions for using the composition(s) of the present invention may appear on the container (such as can, bottle or jar) holding the composition(s) of the present invention or on the box or carton or other packaging comprising the container(s) holding the composition(s).

The compositions described above are useful for application onto keratinous fibers such as hair on the head of human individuals.

Thus, the compositions of the present invention can be made into various cosmetic products such hair care, hair treatment, and hair styling products.

Representative types of hair care compositions, including hair care and styling compositions, of the present invention include compositions for conditioning or protecting hair from heat damage, leave-in hair treatments, rinse-off hair treatments, combination shampoo/styling compositions, hair volumizing compositions, compositions for shaping the hair or maintaining the shape of the hair or styling products (e.g., gels, creams, milks, pastes, waxes, ointments, serums, foams, hair lotions, mousses, pump-sprays, non-aerosol sprays and aerosol sprays).

The compositions of the present invention can be in the form of an aqueous composition or an emulsion, such as a lotion or cream, and in some embodiments may be applied in another form, such as in a serum such as an anhydrous serum (substantially free of water, for example containing less than 0.1% water or not containing added water to the composition).

In one embodiment, the composition of the present invention is in the form of a cream or a lotion or a serum.

In one embodiment, the compositions (first and/or second treatment compositions and/or single treatment composition) of the present invention are in the form of aqueous compositions or aqueous-alcoholic compositions.

In one embodiment, the compositions (first and/or second treatment compositions and/or single treatment composition) of the present invention are in the form of emulsions and further comprise one or more emulusifiers.

The compositions may be packaged in various forms, especially in a tube, a jar or bottles, in pump bottles, in squeeze bottles, or in aerosol containers so as to apply the composition in vaporized form or in the form of a mousse. The compositions may also be impregnated on applicators, especially gloves or wipes.

The composition may be applied by hand, with an applicator nozzle or actuator pump, with a container equipped with a pump, an applicator and a dispensing comb, or with an insoluble substrate impregnated with the composition.

As used herein, the methods and compositions disclosed herein may be used on the hair that has not been artificially dyed, pigmented or permed.

As used herein, the methods and compositions disclosed herein may be also used on the hair that has been artificially dyed, pigmented or permed, relaxed, straightened or other chemical process.

As used herein, the methods and compositions disclosed herein may be also used on the hair that is undergoing a chemical treatment such as a bleaching or lightening treatment or an oxidative dyeing treatment or a relaxing/straightening treatment or a perming/waving treatment.

The compositions according to the disclosure may be prepared according to techniques that are well known to those skilled in the art.

Although the foregoing refers to various exemplary embodiments, it will be understood that the disclosure is not so limited. It will occur to those of ordinary skill in the art that various modifications may be made to the disclosed embodiments and that such modifications are intended to be within the scope of the disclosure. Where an embodiment employing a particular structure and/or configuration is illustrated in the present disclosure, it is understood that the present disclosure may be practiced with any other compatible structures and/or configurations that are functionally equivalent provided that such substitutions are not explicitly forbidden or otherwise known to be impossible to one of ordinary skill in the art.

The following examples are intended to further illustrate the present invention. They are not intended to limit the invention in any way. Unless otherwise indicated, all parts are by weight.

EXAMPLES

The following examples are to illustrate the invention and are non-limiting. In accordance with the various examples, the evaluations and results demonstrate generally that the inventive compositions and methods confer beneficial results, including improved quality of hair and improvement to the hydrophobicity of the hair, including long lasting or wash-resistant hydrophobicity to hair.

TABLE 1

Representative Actives

| Raw Material ("RM") Trade Name or ingredient name or INCI name | Generic Name |
|---|---|
| EPOCROS K-2030-E, 40 wt. % active, supplied by Nippon Shokubai | Oxazoline functionalized polymer A |
| EPOCROS K-2020-E, 40 wt. % active, supplied by Nippon Shokubai | Oxazoline functionalized polymer B |
| LUVIQUAT (13 wt. % active, INCI name: VINYLAMINE/VINYLFORMAMIDE COPOLYMER), supplied by BASF | Polyamine compound |

Hydrophobicity Evaluation on Hair Swatches—Contact Angle Measurements

Hydrophobicity of each swatch was measured via contact angle measurements using Biolin Scientific Contact Angle Tensiometer, Model C204A. A bundle of 30-50 fibers was clamped to create a flat surface. A 3 μL drop of DI (deionized) $H_2O$ was placed on the fiber surface and the contact angle was measured at 10 seconds. The values reported below are an average of 3 measurements using the contact angle at 10 seconds. Natural, undamaged hair is hydrophobic while damaged hair (double bleached, or platinum bleached) is hydrophilic and exhibits a contact angle of 0°.

Example 1

Hydrophobicity Assessments on Hair Treated According to a 1-Step System

The following aqueous solutions were prepared:

Solution 1: 10.0 wt. % EPOCROS RM containing Oxazoline functionalized polymer A (40 wt. % active polymer) in water Solution 2: 10.0 wt. % LUVIQUAT RM (13 wt. % active vinylamine/vinylformamide copolymer) in water Solution 1 and Solution 2 were combined in a weight ratio of 9:1 in order to form a mixture or composition (based on 0.36 g of Solution 1/g of hair plus 0.04 g of Solution 2/g of hair resulting in 0.4 g of the mixture/g of hair).

Platinum bleached hair swatches from International Hair Importers (IHIP) (about 2.0 g each) were washed with a hair cleansing cream, towel dried and treated according to a 1-step application process as follows:

The cleansed hair swatches were contacted or treated with the above mixture or composition containing Solution 1 and Solution 2. The treated hair was massaged for 30 seconds then combed for 15 seconds to ensure even distribution of the mixture. The treated swatches were then heated at about 50° C. for about 40 minutes and air dried overnight at room temperature (RT).

Swatches were washed with 0.4 g of a sulfate-based shampoo/1 g hair and dried. The hydrophobicity of hair (contact angle with the Tensiometer) was measured (T1). The hair swatches were then shampooed with the sulfate-based shampoo and washed four more times (a total of five shampoos or five wash cycles) and the hydrophobicity of the hair was measured after the swatch was dried overnight at RT (T5).

Three measurements (top, middle and end of hair swatch) were acquired for each sample. The average contact angle is reported in the table below with the standard deviation from three measurements.

TABLE 2

| Active Ingredient in RM Sample | Average Contact Angle (°) @ T1 = 1 × Shampoo | Average Contact Angle (°) @ T5 = 5 × Shampoo |
|---|---|---|
| Oxazoline functionalized polymer A | 0.00 | 0.00 |
| Polyamine compound | 81.55 +/− 1.58 | 0.00 |
| Oxazoline functionalized polymer A and Polyamine compound combination* | 121.52 +/− 3.16 | 127.90 +/− 7.73 |

*Amino/Oxazoline (mole ratio) = 1/10.4

The contact angle measurements above show that the combination of oxazoline functionalized polymer A with the polyamine compound, resulted in the formation of a coating on the hair which imparted hydrophobicity or improved hydrophobicity to the hair even after the hair has been shampooed once or five times, i.e., the hydrophobicity imparted to hair was shampoo or wash resistant. In contrast, the results show that the oxazoline functionalized polymer alone did not impart hydrophobicity to hair as shown by the zero contact angle. In addition, the degree of hydrophobicity imparted to hair by the polyamine compound alone was significantly less than that imparted by the inventive combination of oxazoline functionalized polymer and polyamine and this effect did not last after several shampooing or washing cycles as shown by the zero contact angle at T5.

Summary of Findings: In summary, the treatment of the hair with a system comprising an oxazoline functionalized polymer and polyamine compound conferred hydrophobicity benefits or properties to the hair as compared to the treatment of the hair with the oxazoline functionalized polymer alone or the polyamine compound alone. The imparted hydrophobicity benefits were found to be long lasting over several shampooings or shampoo (or wash) resistant.

The treatment composition can also be provided to the hair as a layer by layer system (2-step system or 2-step application process) involving a first composition containing an oxazoline functionalized polymer and a second composition containing a polyamine compound in any sequential order.

The present invention may involve various methods of treating hair with compositions employing various combinations of the oxazoline functionalized polymer A or B in Table 1 with vinylamine/vinylformamide copolymer either as single treatment compositions or according to a 2-step or layer by layer application process.

While the invention has been described with reference to certain exemplary or preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A composition for treatment of keratinous fibers comprising:
at least one oxazoline functionalized polymer; and
at least one polyamine compound;
wherein the at least one oxazoline functionalized polymer is formed by polymerizing monomers having an oxazoline-type functional group of the following formula (I):

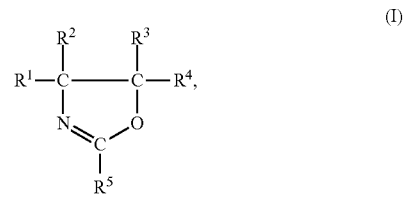

wherein in formula (I),
$R^1$, $R^2$, $R^3$, and $R^4$ represent, independently of each other, hydrogen, a halogen, an alkyl, an aryl, alkoxyalkyl, or alkoxyaryl; and
$R^5$ is an organic group bearing a radical polymerizable vinyl bond.

2. The composition according to claim 1, wherein the at least one oxazoline functionalized polymer is chosen from a waterborne crosslinker polymer, a granule type, or a mixture thereof.

3. The composition according to claim 2, wherein the at least one oxazoline functionalized polymer is a waterborne crosslinker polymer chosen from acrylic-based oxazoline functionalized polymers, styrene/acrylic-based oxazoline functionalized polymers, or a mixture thereof.

4. The composition according to claim 1, wherein the polyamine compound is chosen from non-alkoxylated polyamines, alkoxylated polyamines, or a mixture thereof.

5. The composition according to claim 4, wherein the polyamine compound is a non-alkoxylated polyamine chosen from polyvinylamines, aminated polysaccharides, amine substituted polyalkylene glycols, amine substituted polyacrylate crosspolymers, amine substituted polyacrylates, amine substituted polymethacrylates, amine substituted polyesters, polyamine acids, polyalkylamines, diethylene triamine, triethylenetetramine, spermidine, spermine, aminosilicones having at least two amino groups, or a mixture thereof.

6. The composition according to claim 5, wherein the polyamine compound is chosen from polyvinylamines.

7. The composition according to claim 5, wherein the polyamine compound is chosen from alkoxylated polyamines.

8. The composition according to claim 1, wherein the at least one oxazoline functionalized polymer is present in a concentration, by weight, of from about 0.1% to about 20%, based on the total weight of the composition.

9. The composition according to claim 1, wherein the at least one polyamine compound is present in a concentration, by weight, of from about 0.001% to about 20%, based on the total weight of the composition.

10. The composition according to claim 1, wherein the mole ratio of the oxazoline group(s) of the at least one oxazoline functionalized polymer to the amino group(s) of the at least one polyamine compound is greater than 1.

11. The composition according to claim 1, wherein the mole ratio of the oxazoline group(s) of the at least one oxazoline functionalized polymer to the amino group(s) of the at least one polyamine compound is less than 1.

12. The composition according to claim 1, wherein the mole ratio of the oxazoline group(s) of the at least one oxazoline functionalized polymer to the amino group(s) of the at least one polyamine compound is from between about 80:1 to about 1:80.

13. The composition according to claim 1, further comprising a solvent selected from water, organic solvents, or a mixture thereof.

14. The composition according to claim 1, wherein the keratinous fibers include hair, and wherein the composition is formed in-situ on the hair from a step-wise application on the hair of a first composition comprising the at least one oxazoline functionalized polymer and a solvent, and a second composition comprising the at least one polyamine compound and a solvent, wherein the solvents in the first and second compositions are independently chosen from water, organic solvents, or mixtures thereof.

15. The composition according to claim 1, wherein the composition includes amounts of each of the at least one oxazoline functionalized polymer and the at least one polyamine compound sufficient to impart to the keratinous fibers after application thereto, one or more of hydrophobicity, manageability, and frizz control.

16. The composition according to claim 15, wherein the hydrophobicity imparted to the keratinous fibers includes a contact angle of greater than 85°.

17. The composition according to claim 15, wherein the hydrophobicity imparted to the keratinous fibers confers high humidity curl retention after a period of exposure to humidity ranging from about 40% to 90%.

18. The composition according to claim 15, wherein the hydrophobicity imparted to the keratinous fibers is durable even after one or more wash cycles.

19. A method of treating keratinous fibers, comprising applying onto keratinous fibers, the treatment composition of claim 1.

20. The method according to claim 19, further comprising a step of heating the fibers during, before, and/or after the treatment composition is applied onto the fibers.

21. The method according to claim 19, wherein the method imparts to the keratinous fibers after application thereto, one or more of hydrophobicity, manageability, and frizz control.

22. The method according to claim 21, wherein the method imparts a hydrophobicity to the keratinous fibers resulting in a contact angle of greater than 85°.

23. A method of imparting hydrophobicity and/or manageability to keratinous fibers chosen from hair and/or protecting keratinous fibers chosen from hair from extrinsic damage caused by heating, UV radiation, chemical treatment or mechanical stress, or of repairing a keratinous fiber chosen from hair following extrinsic damage caused by heating, UV radiation, chemical treatment, or mechanical stress comprising: applying to the keratinous fibers a composition according to claim 1; and optionally heating the keratinous fibers; wherein when heating is employed, the composition is applied prior to the heating, during the heating, or after the heating.

24. The method according to claim 23, wherein the method is a process selected from:
a one step process, wherein the composition comprising the at least one oxazoline functionalized polymer and the at least one polyamine compound is provided as a single composition, and is prepared by combining the at least one oxazoline functionalized polymer, the at least one polyamine compound, and at least a solvent, whereby the single composition is applied onto the keratinous fibers;

a one step process, wherein the composition is provided in separate treatment compositions, each separately comprising the at least one oxazoline functionalized polymer and the at least one polyamine compound, the treatment compositions prepared by combining the at least one oxazoline functionalized polymer with at least water to form a first phase, and separately combining the at least one polyamine compound with at least one a solvent selected from water, organic solvents, or a mixture thereof to form a second phase, whereby at the time of use, the phases are combined and agitated to form a mixture that is applied onto the keratinous fibers; and a two-step process, wherein the composition is provided in separate treatment compositions, each separately comprising the at least one oxazoline functionalized polymer and the at least one polyamine compound, the treatment compositions prepared by combining the at least one oxazoline functionalized polymer with water to form a first phase, and separately combining the at least one polyamine compound with at least one a solvent selected from water, organic solvents, or a mixture thereof to form a second phase, whereby at the time of use, each of the phases is applied separately to the keratinous fibers in any order.

25. A system for treating a keratinous fibers comprising one or two separately-contained treatment compositions, the system including:
(a) at least one oxazoline functionalized polymer; and
(b) at least one polyamine compound;
with the proviso that either (a) and (b) are each contained in two separate treatment compositions or (a) and (b) are contained in one treatment composition; and
wherein the at least one oxazoline functionalized polymer is formed by polymerizing monomers having an oxazoline-type functional group of the following formula (I):

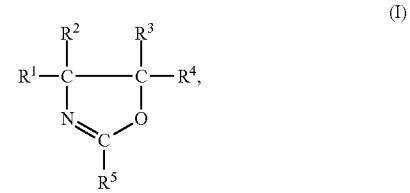

wherein in formula (I),
$R^1$, $R^2$, $R^3$, and $R^4$ represent, independently of each other, hydrogen, a halogen, an alkyl, an aryl, alkoxyalkyl, or alkoxyaryl; and
$R^5$ is an organic group bearing a radical polymerizable vinyl bond.

26. The system according to claim 25, comprising two separately-contained treatment compositions comprising:
(1) a first treatment composition containing:
the at least one oxazoline functionalized polymer in an amount, by weight, of from about 0.1% to about 20%, based on the total weight of the first treatment composition; and
at least one solvent; and
(2) a second treatment composition comprising:
the at least one polyamine compound, in an amount, by weight, of from about 0.04% to about 20%, based on the total weight of the second treatment composition; and
at least one solvent.

27. The system according to claim 25, comprising one treatment composition comprising:
- the at least one oxazoline functionalized polymer in an amount, by weight, of from about 0.1% to about 20%, based on the total weight of the treatment composition;
- the at least one polyamine compound in an amount, by weight, of from about 0.001% to about 20%, based on the total weight of the treatment composition.

28. A method of treating keratinous fibers, wherein the method is a two-step process comprising the steps of:
- (i) applying the first treatment composition of claim 26 onto the fibers;
- (ii) applying the second treatment composition of claim 26 onto the fibers; and
- (iii) optionally, heating the fibers at a temperature above room temperature;
- wherein the keratinous fibers include hair.

29. A method of treating keratinous fibers, comprising applying the treatment composition of claim 27 onto the fibers; wherein the keratinous fibers include hair; and optionally, heating the fibers at a temperature above room temperature.

* * * * *